United States Patent [19]
Andreiko et al.

[11] Patent Number: 5,456,600
[45] Date of Patent: Oct. 10, 1995

[54] COORDINATED ORTHODONTIC ARCHWIRES AND METHOD OF MAKING SAME

[75] Inventors: Craig A. Andreiko, Alta Loma; Mark A. Payne, Whittier, both of Calif.

[73] Assignee: Ormco Corporation, Glendora, Calif.

[21] Appl. No.: 285,961

[22] Filed: Aug. 4, 1994

Related U.S. Application Data

[63] Continuation-in-part of Ser. No. 973,973, Nov. 9, 1992, Pat. No. 5,431,562.

[51] Int. Cl.$^6$ .................................................... A61C 3/00
[52] U.S. Cl. ................................................ 433/24; 433/20
[58] Field of Search ............................ 433/24, 8, 9, 16, 433/17, 20

[56] References Cited

U.S. PATENT DOCUMENTS

| | | | |
|---|---|---|---|
| 5,011,405 | 4/1991 | Lemchem | 433/24 |
| 5,139,419 | 8/1992 | Andreiko et al. | 433/24 |

OTHER PUBLICATIONS

Catalog: Ormco Orthodontic Products, pub. by Ormco Corporation, 1990, Section 5.
Catalog: 3M Unitek Orthodontic Product, pub. by 3M, pp. 5–1 to 5–7.
Catalog: Rocky Mountain Orthodontics Cat. #4, pub. by RMO, Inc., pp. G6–G9.
Catalog: Orthodontics pub. by Dentaurum, Inc., pp. 90–98.

*Primary Examiner*—Cary E. O'Connor
*Attorney, Agent, or Firm*—Wood, Herron & Evans

[57] ABSTRACT

Coordinated orthodontic archwires are provided based on a method of designing custom orthodontic appliances based in individual patient anatomy and, based on a plurality of such custom designs, designing and manufacturing a standardized appliance for patients of average dental anatomy. From such method, a relationship is established for coordinating one archwire to another of any given design. The coordinated archwires so provided include an upper archwire that is an expansion of a lower archwire, and in addition, when the shapes of the archwires are superimposed, are spaced apart more in the vicinity of the cuspids and first bicuspids than in the vicinity of the incisors and, preferably, also the second bicuspids. The spacing difference is at least 0.005 inches, particularly for an appliance with low profile brackets, and is up to 0.025 or 0.035 inches for an appliance with the more conventional brackets. The spacings are determined as a function of the length of the wire from the midline of the wire.

20 Claims, 3 Drawing Sheets

COORDINATED ORTHODONTIC ARCHWIRES AND METHOD OF MAKING SAME

This application is a continuation-in-part of U.S. patent application Ser. No. 07/973,973, filed Nov. 9, 1992, entitled Method and Apparatus for Designing and Forming a Custom Orthodontic Appliance and for the Straightening of Teeth Therewith, now U.S. Pat. No. 5,431,561.

This application is related to the applicants' commonly assigned U.S. patent applications, filed herewith, entitled "Low Profile Orthodontic Appliance" and "Orthodontic Appliance Providing for Mesial Rotation of Molars".

The above identified U.S. patent applications of applicants are hereby expressly incorporated by reference herein.

FIELD OF THE INVENTION

The present invention relates to orthodontic appliances used for the straightening of the teeth of patients and particularly to archwires for orthodontic appliances that are secured to both the upper and lower arches of a patient's teeth.

BACKGROUND OF THE INVENTION

In current orthodontic practice, the teeth of patients are straightened through the use of orthodontic appliances made up of sets of orthodontic brackets, each of which is secured to one of the individual teeth of the patient. Each of the brackets connects the tooth to an orthodontic archwire which is mounted on the upper or lower arch of the patients teeth by the brackets. Most commonly, the appliance includes one set of upper brackets that specially configured for attachment to the surfaces of the upper teeth and interconnected by an upper archwire, and a set of lower brackets that are specially configured for attachment to the lower teeth and interconnected by a lower archwire.

The archwires that are used in such orthodontic appliances generally have an arcuate shape that corresponds to some archform designed to cooperate with the set of brackets to which they are attached to facilitate the movement of the patient's teeth to some dental archform that the patient's teeth are expected to assume when straightened. Archwires of a large number of preformed shapes are available to the orthodontist. Some archwires are configured for use on the upper teeth of the patient while other archwires are configured for use on the lower teeth of the patient. Each shape has advocates among orthodontic authorities and each has situations or types of treatment for which its use is intended by its designers or preferred by practitioners. The varying anatomies of patients, the variations in bracket designs selected by the practitioner and the particular treatment plan prescribed by the orthodontist affect the selection of archwire shape. Further, the orthodontist's training, experience and treatment theories have a bearing on the archwires that a particular orthodontist will select for treatment of a given case.

In all situations, however, when the application of all of the selection criteria results in the selection of an archwire for either the upper or lower arch of a patient, the wire, when installed by the orthodontist on brackets on the teeth of the patient, cooperates with the brackets to move the teeth toward desired finish positions on the respective dental arch. Because the desired finish positions for the teeth on each of the arches of the patient are positions in which the upper and lower teeth occlude in a predetermined manner, it is incumbent upon the orthodontist to select upper and lower archwires that will cooperate with the respective sets of brackets to move the upper and lower teeth of the particular patient into proper occlusion.

One of the problems encountered in the prior art in the selection of archwires to function in a coordinated manner in a given orthodontic appliance is that the archwires are usually designed produce a preferred dental archform of the teeth in a particular arch, maxillary or mandibular, for which the archwire is designed, or to satisfy some treatment concept for one or the other arch. Most archwire designs, however, have not adequately considered the requirements imposed by the treatment objectives for the teeth of the opposing arch. As a result, archwires that appear to be ideal for treatment of the teeth of a particular arch are found to have no equally effective functional counterpart that is equally ideally suited for the treatment of the other arch, when the two archwires are used together.

Accordingly, there is a compelling need for a method of coordinating the shapes of upper and lower orthodontic archwires. There is a particular need for coordinated sets of orthodontic archwires that can be made available to provide orthodontists with coordinated sets of archwires from which to choose.

SUMMARY OF THE INVENTION

It is a primary objective of the present invention to provide a method of coordinating the upper and lower archwires of an orthodontic appliance. It is also a primary objective of the present invention to provide coordinated pairs of archwires for use in orthodontic appliances.

Applicants have proposed, in their parent U.S. patent application Ser. No. 07/973,973, to produce custom orthodontic appliances for individual patients by digitizing the shapes of the patient's teeth and jaw and calculating an ideal occlusion in which the teeth of each specific patient will be placed in ideal finish positions. Based on these ideal calculated finish positions for the specific patient, a custom appliance is designed and manufactured automatically, based on the calculated occlusion, that move the patient's teeth to the ideal finish positions. For such an appliance, brackets and archwires of custom geometries are produced that are coordinated to work together to achieve the intended treatment result. The custom appliance so produced will be ideal for the treatment of the particular patient from whom the tooth and jaw shape data was initially taken In accordance with certain principles of the present invention, standardized pairs of coordinated archwires and the relationships between the archwires of such pairs are established by correlation of the shapes of archwires of such custom orthodontic appliances produced by applicants' custom appliance design method for a large population of patients and for statistical groups of patients. As a result, applicants have provided a method of coordinating archwire pairs for standardized orthodontic appliances that will be useful in the treatment of a large number of patients of the population or population group.

In accordance with the preferred embodiment of the present invention, there is provided a pair of archwires for mounting on the buccal-labial surfaces of the teeth of a patient in which the shapes of the upper and lower archwires of each coordinated pair have curvature radii that are interrelated by the addition of a component that varies in a particular manner as a function of the arch length of the archwire. More particularly, the upper archwire of each coordinated pair is larger than the lower archwire of such pair, such that, when one wire is centered and superimposed on the other archwire of the coordinated pair will be spaced a distance measured perpendicular to the wire at various points along the length of the wire. Preferably, the spacing is maintained at or in the vicinity of the bracket connection points of each of the wires.

In the preferred embodiment of the invention, the upper archwire is larger than the lower archwire and spaced therefrom an average of approximately 0.08 inches, plus or minus approximately 0.01 inches for treatment of a majority of patients. The spacing of the wires is less in the vicinity of the centrals and laterals ("front teeth"), where it is the smallest than in the vicinity of the cuspids and first bicuspids ("side teeth"), where it is the largest. The difference in spacing varies from up to 0.025 to 0.035 when used with most of the brackets currently being used, to as low as approximately 0.005 to 0.010 inches when used with applicants' low profile appliance, which is preferred, in which the lower archwire is maintained within 0.050 or less of each of the teeth.

The coordination of archwires in accordance with the principles of the present invention is based in part on the concept of quantizing the shapes of teeth for the patients for whom the appliance is designed, calculating finish positions for such teeth including the constructing of an occlusion by which the ideal finish positions of the upper and lower teeth of the patients are related, and designing an optimal appliance based on the shape of the teeth and the ideally occluding tooth finish positions.

When, in the manufacture or selection of an orthodontic appliance, archwires are coordinated according to the relationships of the present invention, the likelihood of producing a finished orthodontic result that places the teeth of the upper and lower arches of a patient in proper occlusion is increased. The selection by an orthodontist of an archwire for one arch that is judged best for the patient and the treatment plan selected will be supplemented, by the coordination process of applicants, by the provision of a coordinated archwire for the other arch, either upper or lower, that is related to the other archwire by a relationship that is based on the anatomical dimensions of the teeth and the proper way the teeth are to occlude.

These and other objectives and advantages of the present invention will be more readily apparent from the following detailed description of the drawings and preferred embodiments, in which:

DETAILED DESCRIPTION OF THE PREFERRED EMBODIMENTS

In accordance with the principles of the present invention, archwires are coordinated based in part on the concept quantizing shapes of teeth for the patients for whom the appliance is designed, calculating finish positions for such teeth including the constructing of an occlusion by which the ideal finish positions of the upper and lower teeth of the patients are related, and designing an optimal appliance based on the shape of the teeth and the ideally occluding tooth finish positions. Preferably, the process is performed digitally in a computer programmed in accordance with the methods described in detail in applicants copending U.S. patent applications Ser. No. 07/973,973, filed Nov. 9, 1993, entitled Method and Apparatus for Designing and Forming a Custom Orthodontic Appliance and for the Straightening of Teeth Therewith, and U.S. patent applications, filed herewith, entitled "Low Profile Orthodontic Appliance" and "Orthodontic Appliance Providing for Mesial Rotation of Molars", which are incorporated by reference herein.

The methods set forth in applicants' prior applications referred to above include processes for designing and manufacturing orthodontic appliances on an individual patient basis, based in digital tooth and jaw shape data taken from the individual patient to construct an ideal occlusion and design an appliance for the individual patient. The coordination of archwires suitable for large numbers of patients is carried out, in the preferred embodiment of the present invention, by averaging or otherwise statistically correlating the results of a number of such individualized custom cases.

Figure 1:
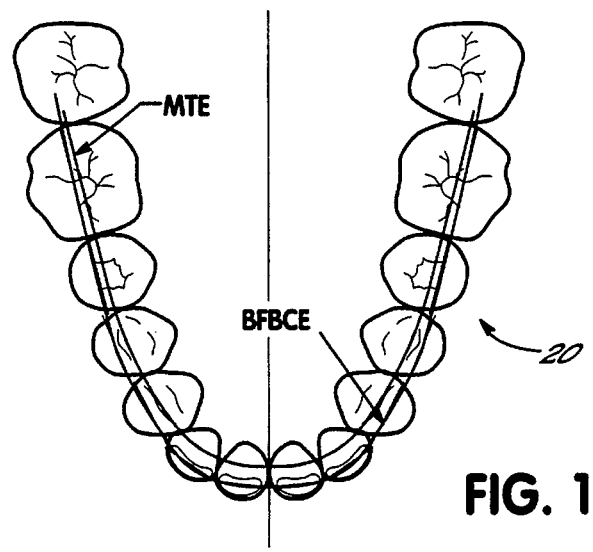
FIG. 1 is a top plan diagram of mandibular teeth of a patient in ideal finish positions in relation to certain archforms.

In accordance with the methods set forth in applicants' prior applications referred to above, a computer based model of the finish positions of the mandibular teeth of the individual as well as the statistically average patients may be considered as represented by the diagram of FIG. 1, in which the mandibular teeth 20 of the patient are illustrated in relation to two mathematical curves. The two mathematical curves include a first curve representing the cortical bone of the lower jaw of the patient which confines the roots of the lower teeth, which curve applicants refer to as the mandibular trough equation MTE. The second curve, which represents a statistical best fit curve through the locations of the prominent tips of the lower teeth 20 of the patient, applicants refer to as the best fit buccal cusp equation BFBCE.

Figure 2:
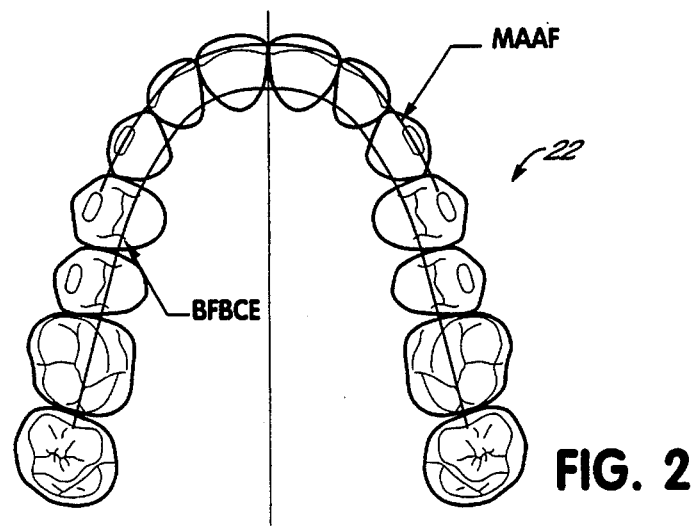
FIG. 2 is a bottom plan diagram of maxillary teeth of a patient in ideal finish positions in relation to certain archforms.

Further in accordance with the methods set forth in applicants' prior applications referred to above, the computer based model of the finish positions of the maxillary teeth of the patient may be considered as represented by the diagram of FIG. 2, in which the maxillary teeth 22 of the patient are illustrated in relation to the mathematical curve BFBCE, as well as another curve, which applicants refer to as the maxillary anterior archform equation MAAF, that defines the positions of the lingual surfaces of the maxillary anterior teeth and which is related to the MTE and BFBCE by certain dimensions of the patient's teeth.

Figure 3:
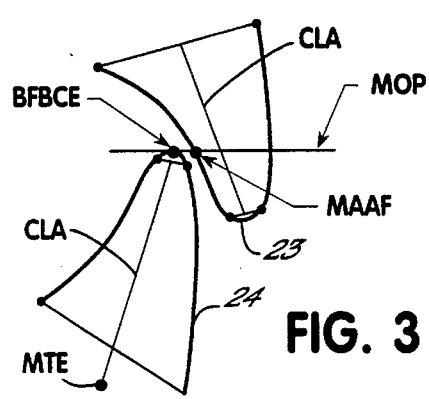
FIG. 3 is a profile diagram viewing, in a distal direction along the arches, upper and lower laterals in occlusion when positioned in accordance with FIGS. 1 and 2, respectively.
Figure 4:
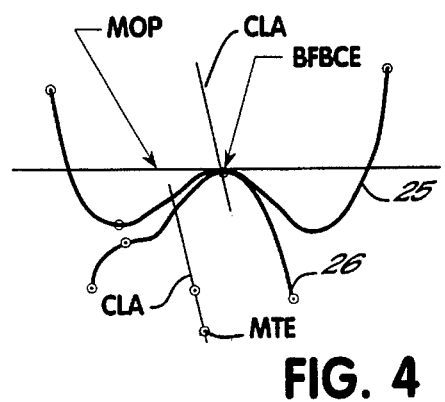
FIG. 4 is a profile diagram viewing, in a distal direction along the arches, upper and lower first bicuspids in occlusion when positioned in accordance with FIGS. 1 and 2, respectively.

When the lower and upper teeth are respectively positioned in their finish positions and in proper occlusion, corresponding upper and lower teeth are in a particular relationships. Such relationships are illustrated for representative front teeth, by profiles of the upper and lower laterals 23 and 24, respectively, viewed in a mesial to distal direction, in FIG. 3. The profiles of the teeth 23 and 24 are therein illustrated in relation to the archforms MTE, BFBCE and MAAF. and also in relation to a plane of occlusion MOP, on which, in a top view, preferably lie the incisal tips of the lower anterior teeth, the buccal cusps tips of the lower bicuspids and mesial buccal cusp tips of the lower molars. A similar representation of the profiles of certain side teeth, for example the first bicuspids 25 and 26, is illustrated in FIG. 4. In FIGS. 3 and 4, the crown long axes CLAs of the teeth are shown in relation to the profiles of the teeth.

Figure 5:
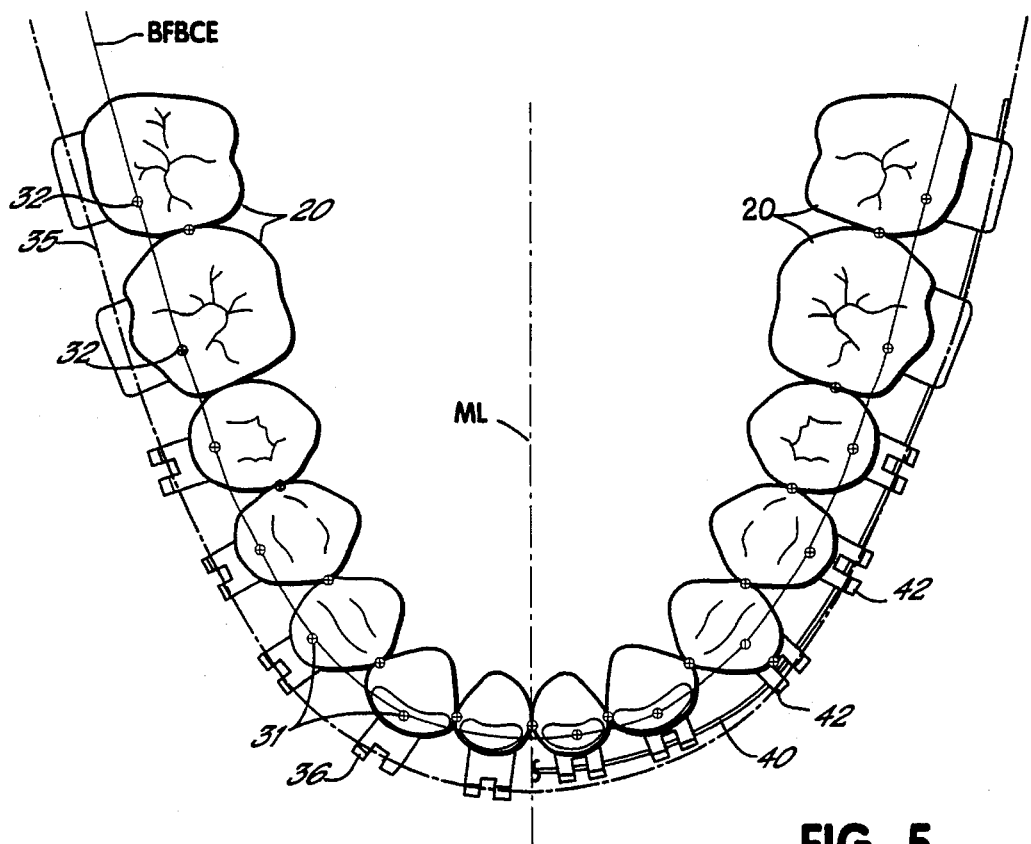
FIG. 5 is a plan view diagram of the mandibular teeth of a patient illustrating standard and low profile archwires.

When the positioning and occlusion of the teeth are constructed, an appliance is designed. Such a design results in sets of brackets, including one for each of the teeth, and archwires, including one for each of the upper and lower arches of teeth. The brackets and archwires, as for the lower teeth 20 for example, may be represented by one of the designs illustrated in the diagram of FIG. 5. In FIG. 5, the lower teeth 20 are illustrated with the incisal tips 31 of the lower anterior teeth and the mesial buccal and buccal cusp tips 32 of the molars and bicuspids, respectively, lying on the dental archform equation BFBCE. In the prior art, archwires were intended to conform to shapes of the dental archform of the teeth with the wire spaced equidistant therefrom. A curve 35, representing the shape of such an archwire, is illustrated. Such an archwire is supported by brackets 36 that typically space the archwire up to 0.075 inches or more from the surfaces of at least most of the teeth. Applicants prefer the archwire shape of their low profile appliance described in their related patent application identified above, which is illustrated by the archwire 40 in FIG. 5. Such an archwire 40 converges with the archform BFBCE at the front of the mouth, and is supported on the teeth on low profile brackets 42, which space the archwire 40 from the tooth, measured from the centerline of the archwire to the surface of the tooth in the plane of the archwire, by a distance of approximately 0.035 to 0.050 inches for padless brackets with bonding pads, and 0.025 to 0.035 inches for brackets wherein the slotted support is bonded directly to the surface of the tooth. A similar difference in archwire shape between what is conventional and what is preferred by applicants occurs, but less dramatically, for the upper teeth. Both the traditional appliance archwires and applicants' low profile archwires can be coordinated in accordance with principles of the present invention.

Figure 6:
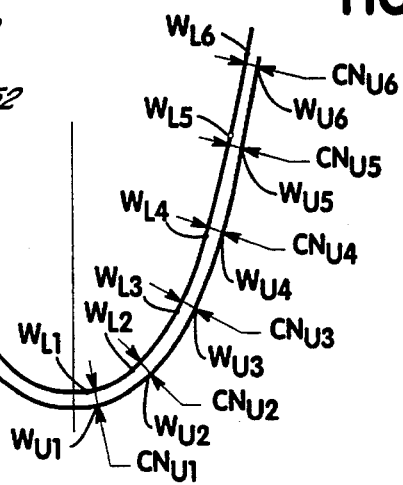
FIG. 6 is a plan view diagram illustrating superimposed upper and lower archwires coordinated in accordance with principles of the present invention.

By use of the tooth shape and occlusion based archwire design method referred to above, upper and lower archwire shapes are developed, as for example are illustrated as archwires 50 and 52. respectively, in FIG. 6. Referring to FIG. 6, the arch length from the midline ML of the mouth to a line normal to the midpoint of each of the teeth at which each of the brackets 36 or 42 connects is calculated. The intersections of these normal lines with the archwires 50 and 52 are indicated as the points W, designated as $W_{UI}$ and $W_{LI}$, respectively, for the upper and lower teeth, where I refers to the tooth, with I=1 representing a central, I=2 representing a lateral, . . . , I=6 representing a first molar. The distances between adjacent points along the upper archwire 50,ML, $W_{U1'}$ . . . , $W_{U6'}$ and each of the points along the lower archwire 52, ML, $W_{L1'}$ . . . , $W_{L6''}$ are represented, respectively, in Tables 1 and 2 for average Caucasian patients, and in Tables 3 and 4 for average Asian patients, which contain additional statistics on measurement distributions among the patients evaluated.

TABLE 1

The Caucasian Mandibular Archwire Chord Lengths

|  | Molar | 2 Bicus | 1 Bicus | Cuspid | Lateral | Central | Arch Len |
| --- | --- | --- | --- | --- | --- | --- | --- |
| Average | 0.3881 | 0.3217 | 0.3072 | 0.3101 | 0.2602 | 0.1235 | 0.7108 |
| Std. Dev | 0.0212 | 0.0190 | 0.0195 | 0.0187 | 0.0201 | 0.0118 | 0.0778 |
| Range | 0.1094 | 0.0895 | 0.1036 | 0.0952 | 0.0967 | 0.0532 | 0.4001 |
| Max | 0.4531 | 0.3622 | 0.3411 | 0.3626 | 0.3093 | 0.1482 | 1.9152 |
| Min | 0.3437 | 0.2727 | 0.2375 | 0.2674 | 0.2127 | 0.0950 | 1.5151 |

TABLE 2

The Caucasian Maxillary Archwire Chord Lengths

|  | Molar | 2 Bicus | 1 Bicus | Cuspid | Lateral | Central | Arch Len |
| --- | --- | --- | --- | --- | --- | --- | --- |
| Average | 0.3592 | 0.2978 | 0.3291 | 0.3321 | 0.3609 | 0.1923 | 1.8714 |
| Std. Dev | 0.0172 | 0.0171 | 0.0188 | 0.0200 | 0.0238 | 0.0138 | 0.0789 |
| Range | 0.1018 | 0.0868 | 0.1093 | 0.1120 | 0.1442 | 0.0740 | 0.4474 |
| Max | 0.4186 | 0.3409 | 0.3747 | 0.4014 | 0.4527 | 0.2425 | 2.1602 |
| Min | 0.3168 | 0.2541 | 0.2654 | 0.2894 | 0.3084 | 0.1685 | 1.7128 |

TABLE 3

The Asian Mn archwire chord lengths.

|  | Molar | 2 Bicus | 1 Bicus | Cuspid | Lateral | Central | Arch Len |
|---|---|---|---|---|---|---|---|
| Average | 0.3182 | 0.3315 | 0.3058 | 0.3105 | 0.2642 | 0.1267 | 1.6568 |
| Std. Dev | 0.0198 | 0.0228 | 0.0212 | 0.0205 | 0.0161 | 0.0102 | 0.0821 |
| Range | 0.1027 | 0.1096 | 0.1154 | 0.0917 | 0.0753 | 0.0426 | 0.4093 |
| Max | 0.3837 | 0.3861 | 0.3543 | 0.3564 | 0.2965 | 0.1456 | 1.8400 |
| Min | 0.2810 | 0.2766 | 0.2389 | 0.2647 | 0.2212 | 0.1030 | 1.4306 |

TABLE 4

The Asian Maxillary Archwire Chord Lengths

|  | Molar | 2 Bicus | 1 Bicus | Cuspid | Lateral | Central | Arch Len |
|---|---|---|---|---|---|---|---|
| Average | 0.3182 | 0.3315 | 0.3058 | 0.3105 | 0.2642 | 0.1267 | 1.6568 |
| Std. Dev | 0.0198 | 0.0228 | 0.0212 | 0.0205 | 0.0161 | 0.0102 | 0.0821 |
| Range | 0.1027 | 0.1096 | 0.1154 | 0.0917 | 0.0753 | 0.0426 | 0.4093 |
| Max | 0.3318 | 0.3524 | 0.3982 | 0.3868 | 0.4061 | 0.2276 | 2.0776 |
| Min | 0.2624 | 0.2492 | 0.3052 | 0.3009 | 0.2990 | 0.1642 | 1.6611 |

With the points W defined, the spacing between the lower archwire 52 and upper archwire 50 is determined at each of the points W. For applicants' preferred low profile appliance, the spacings of the archwires measured perpendicular to the maxillary archwire at each of the points $W_{UI}$ are set forth in Table 5 for Caucasian patients and in Table 6 for Asian patients.

TABLE 5

The Caucasian Maxillary Coordination Numbers (CNs)

|  | Central | Lateral | Cuspid | 1 Bicus | 2 Bicus | Molar |
|---|---|---|---|---|---|---|
| Average | 0.0743 | 0.0751 | 0.0843 | 0.0850 | 0.0770 | 0.0782 |
| Std. Dev | 0.0153 | 0.0131 | 0.0125 | 0.0127 | 0.0135 | 0.0154 |
| Range | 0.0692 | 0.0811 | 0.0661 | 0.0650 | 0.0672 | 0.1137 |
| Max | 0.1133 | 0.1134 | 0.1162 | 0.1262 | 0.1116 | 0.1176 |
| Min | 0.0441 | 0.0323 | 0.0501 | 0.0612 | 0.0444 | 0.0439 |

TABLE 6

The Asian Maxillary Coordination Numbers (CNs)

|  | Central | Lateral | Cuspid | 1 Bicus | 2 Bicus | Molar |
|---|---|---|---|---|---|---|
| Average | 0.077 | 0.0747 | 0.0829 | 0.0891 | 0.0811 | 0.0827 |
| Std. Dev | 0.0131 | 0.0118 | 0.0118 | 0.0109 | 0.0120 | 0.0183 |
| Range | 0.0603 | 0.0543 | 0.0633 | 0.0440 | 0.0519 | 0.0847 |
| Max | 0.1116 | 0.1038 | 0.1181 | 0.1114 | 0.1091 | 0.1331 |
| Min | 0.0513 | 0.0496 | 0.0548 | 0.0674 | 0.0572 | 0.0485 |

These numbers are what applicants refer to as the maxillary coordination numbers $CN_U$. Similar measurements from the mandibular archwire 52 to the maxillary archwire 52, measured at the points $W_{LI}$ along the lower archwire 52, may alternatively or in addition be used. Such mandibular coordination numbers are close in value to the corresponding maxillary numbers.

With the above tabulated data, given an upper archwire of a desired shape, a lower coordinated archwire can be produced, and given a lower archwire of a desired shape, an upper coordinated archwire can be produced.

Figure 7:
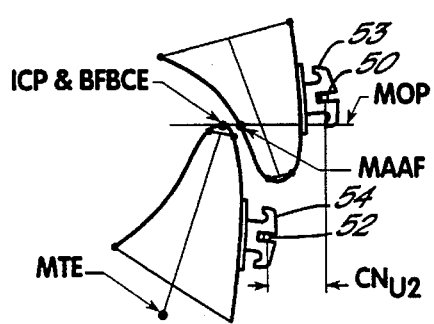
FIG. 7 is a diagram similar to FIG. 3 illustrating upper and lower laterals with an appliance mounted thereon.
Figure 8:
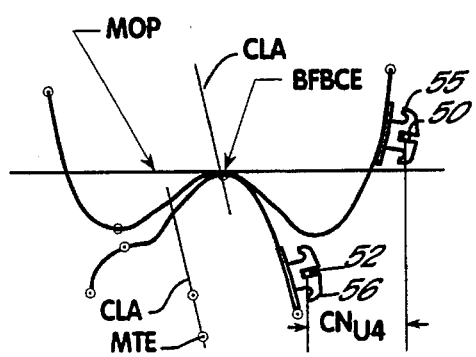
FIG. 8 is a diagram similar to FIG. 4 illustrating upper and lower laterals with an appliance mounted thereon.

The coordination numbers CN can be understood further by reference to the diagrams of FIGS. 7 and 8, which correspond to FIGS. 3 and 4, and illustrate the spacing of the upper and lower archwires 50 and 52 supported on upper and lower brackets 53 and 54, and 55 and 56, adjacent the laterals and first bicuspids, respectively. The maxillary coordination numbers illustrated, $CN_{U1'}$ . . . , $CN_{U6'}$ is the distance in inches, measured perpendicular to one of the wires at a point $W_U$ between the lower archwire 52 and the upper archwire 50. The figures show how the coordination number is related to the tooth shape, the archform equations MTE, BFBCE and MAAF, and the positioning of the teeth in relation to the archform equations and each other.

The digital process described above and in the applicants' prior patent applications results in the generation of digital records representing the equation of the shape of the designed archwires. Such information is preferably converted to numerically controlled machine control signals that are used to operate a wire forming machine to produce the archwires of the calculated coordinated shapes. Such wire forming machines may be those of the wire bending type described in applicants copending U.S. patent application Ser. No. 07/973,947 entitled "Custom Orthodontic Archwire Forming Method and Apparatus", filed Nov. 9, 1992, expressly incorporated herein by reference. For other applications, the use of a heat treated wire is preferred.

Figure 9:
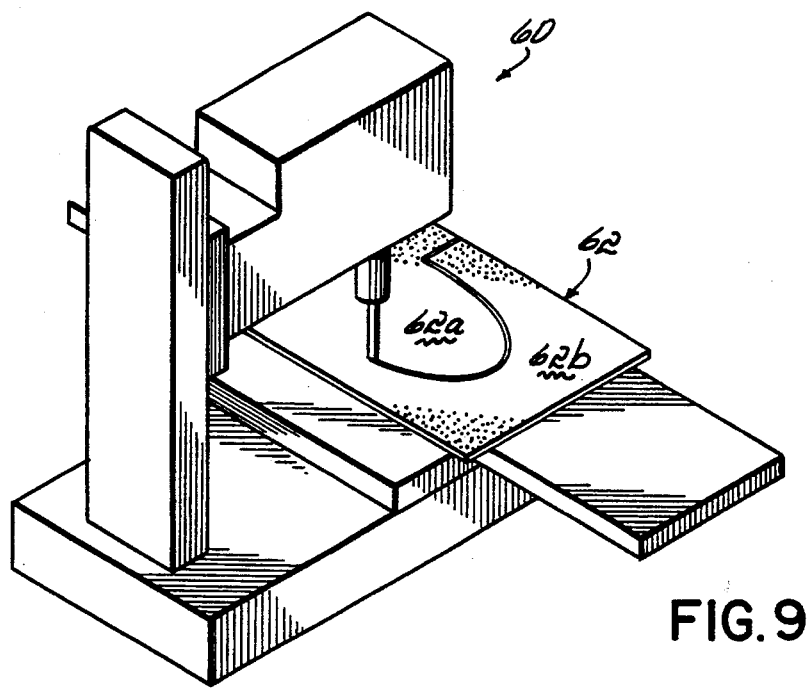
FIG. 9 is a perspective diagram illustrating one embodiment of an apparatus for automatically cutting an archwire forming template for use in accordance with the present invention.
Figure 10:
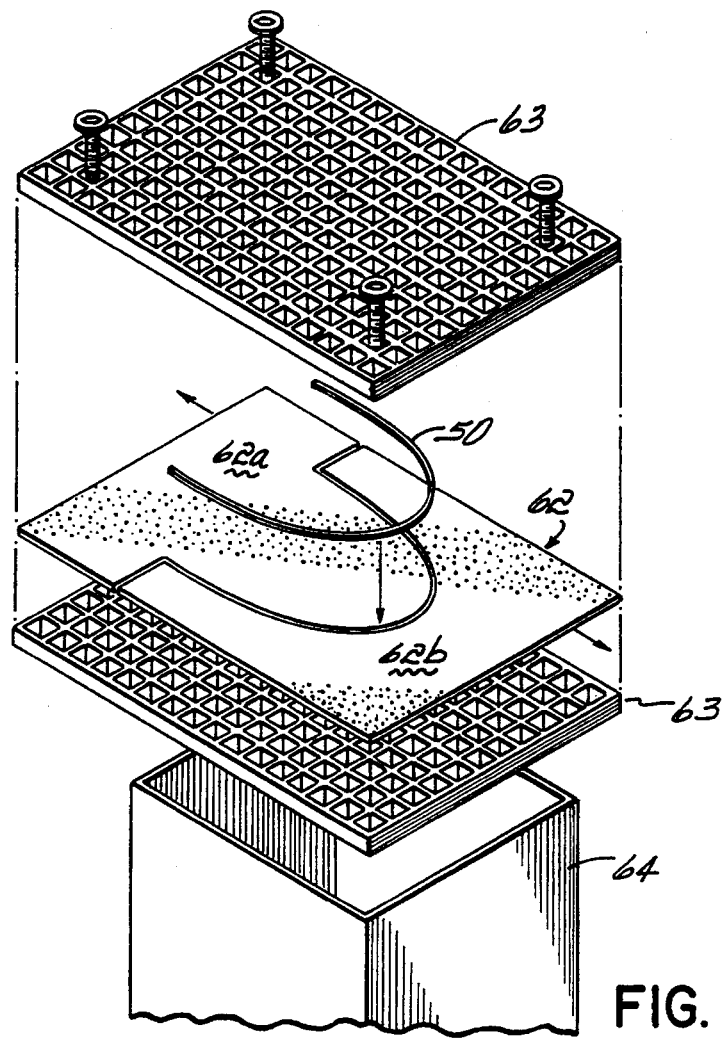
FIG. 10 is a perspective diagram illustrating the formation of an archwire with the template of FIG. 9.

A heat treated or heat formed wire is preferably produced by generating a milling machine code and driving a machine 60 therewith to cut the contour of the archwire to be formed in a template 62, as illustrated in FIG. 9. The template 62 is cut in a material, such as a 0.01 inch thick heat tolerant rigid foam material. Then, the template 62 is separated into two parts 62a and 62b, and the milled surfaces are used on a plate-like clamp fixture to confine between the template parts 62a and 62b the archwire forming wire material that will form, for example the archwire 50, as illustrated in FIG. 10. The wire material is, so confined, is heated to some annealing or other such processing temperature, of, for example, 500° C., by a heater 64, to permanently set the wire to the shape of the contour milled in the template 62.

From the above, particularly the detailed description of the invention, it will be apparent to those skilled in the art that modifications, additions and adaptations of the inven- The following is presently claimed:

1. A method of forming an orthodontic archwire of a shape coordinated to the shape of a predefined archwire of an opposing upper or lower arch, the method comprising the steps of:
   (a) determining the shape of the predefined archwire for a first one of the upper or lower arches of teeth of a patient;
   (b) locating points along the length of the predefined archwire at which the archwire connects to orthodontic brackets mounted on the teeth of a patient, the points including a point for connection to brackets mounted, in order, on a central, a lateral, a cuspid, a first bicuspid, a second bicuspid and a first molar;
   (c) forming a coordinated archwire of a second and opposite one of the upper or lower arches of the teeth of a patient such that one of the archwires is a lower archwire for the lower arch and the other archwire is an upper archwire for the upper arch, the coordinated archwire having a shape defined such that:
      (i) the upper archwire, in the vicinity of each of the located points, is spaced outwardly from lower archwire a coordinated distance,
      (ii) the coordinated distance being the least at the point for connection to brackets mounted on the central or lateral and the greatest at the point for connection to brackets at the cuspid or bicuspid, the coordinated distance with is the greatest being at least 0.005 inches greater than the coordinated distance that is the least.

2. The method of claim 1 wherein:
the locating step includes the step of determining a midpoint on the predefined archwire, the predefined archwire being symmetrical about the midpoint;
the coordinated distance being the least in the range of 0.12 to 0.55 inches from the midpoint of the predefined archwire and being the greatest in the range of 0.70 to 1.12 inches from the midpoint of the predefined archwire.

3. The method of claim 1 wherein:
the coordinated distance that is the greatest being not more than approximately 0.025 inches greater than the coordinated distance that is the least.

4. The method of claim 1 wherein:
the coordinated distance that is the greatest being not more than approximately 0.035 inches greater than the coordinated distance that is the least.

5. The method of claim 1 wherein:
the coordinated distance being the greatest at the located point for connection to a bracket for mounting on the first bicuspid.

6. A method of forming a coordinated pair of orthodontic archwires comprising the steps of:
   (a) forming an upper and a lower archwire for respective upper and lower arches of teeth of a patient;
   (b) at points along the length of one of the archwires at which the archwire connects to orthodontic brackets mounted on the teeth of one of the arches of a patient, the points including a point for connection to brackets mounted, in order, on a central, a lateral, a cuspid, a first bicuspid, a second bicuspid and a first molar:
      (i) the upper and lower archwires being shaped such that the upper archwire is spaced, in the vicinity of each of the points, outwardly from the lower archwire a coordinated distance,
      (ii) the coordinated distance being the least at the point for connection to a bracket mounted on the central or lateral and the greatest at the point for connection to a bracket at the cuspid or bicuspid, the coordinated distance that is the greatest being at least 0.005 inches greater than the coordinated distance that is the least.

7. The method of claim 6 wherein:
the archwires are symmetrical about a midpoint thereof;
the coordinated distance being the least in the range of 0.12 to 0.55 inches from the midpoint of the archwires and being the greatest in the range of 0.70 to 1.12 inches from the midpoint of the archwires.

8. The method of claim 6 wherein:
the coordinated distance that is the greatest being not more than approximately 0.025 inches greater than the coordinated distance that is the least.

9. The method of claim 6 wherein:
the coordinated distance that is the greatest being not more than approximately 0.035 inches greater than the coordinated distance that is the least.

10. The method of claim 6 wherein:
the coordinated distance being the greatest at a point for connection to a bracket for mounting on the first bicuspid.

11. The method of claim 6 wherein:
the archwires are spaced from 0.07 to 0.09 inches along their lengths.

12. The method of claim 6 wherein:
the archwires are most closely spaced in the range of within 0.55 inches from the midpoint and most greatly spaced in the range of 0.70 to 1.12 inches from the midpoint.

13. The method of claim 6 wherein:
the archwires are spaced less than 0.08 inches in the range of 0.12 to 0.55 inches from the midpoint and spaced more than 0.80 in the range of 0.70 to 1.12 inches from the midpoint.

14. A coordinated pair of orthodontic archwires comprising:
an upper archwire and a lower archwire; each of the archwires having a generally planar arcuate shape that is symmetrical about a centerline;
the arcuate shape of the upper archwire being larger than the arcuate shape of the lower archwire such that, when superimposed on their respective centerlines, the upper archwire is outwardly spaced from the lower archwire along its entire length;
there being a point along the lengths of the archwires in the range of 0.12 to 0.55 inches from the centerline that is spaced at least 0.005 inches less than a point along the lengths of the archwires in the range of 0.70 to 1.12 inches from the centerline.

15. The archwires of claim 14 wherein:
the archwires are spaced from 0.07 to 0.09 inches along their lengths.

16. The archwires of claim 14 wherein:
the archwires being most closely spaced in the range of 0.12 to 0.55 inches from the centerline and most greatly spaced in the range of 0.70 to 1.12 inches from the centerline.

17. The archwires of claim 14 wherein:
the archwires being spaced less than 0.08 inches in the range of 0.12 to 0.55 inches from the centerline and spaced more than 0.80 inches in the range of 0.70 to 1.12 inches from the centerline.

18. The archwires of claim 14 wherein:

the archwires being spaced at their greatest distance not more than approximately 0.025 inches more than they are spaced at their closest distance.

19. The archwires of claim 14 wherein:

the archwires being spaced at their greatest distance not more than approximately 0.035 inches more than they are spaced at their closest distance.

20. The archwires of claim 14 wherein:

there is a point along the lengths of the archwires in the range of 1.37 to 1.47 inches from the centerline that is spaced less than a point along the lengths of the archwires in the range of 0.70 to 1.12 inches from the centerline.

* * * * *

UNITED STATES PATENT AND TRADEMARK OFFICE
CERTIFICATE OF CORRECTION

PATENT NO. : 5,456,600
DATED : October 10, 1995
INVENTOR(S) : Craig A. Andreiko, et al.

It is certified that error appears in the above-indentified patent and that said Letters Patent is hereby corrected as shown below:

Column 9, line 31, "with" should be --that--.

Column 10, line 44, ";" should be --,--.

Signed and Sealed this

Sixteenth Day of July, 1996

Attest:

BRUCE LEHMAN

Attesting Officer     Commissioner of Patents and Trademarks